(12) United States Patent
McKay et al.

(10) Patent No.: US 8,591,935 B2
(45) Date of Patent: *Nov. 26, 2013

(54) METHODS AND COMPOSITIONS FOR TREATING PAIN COMPRISING A STATIN

(75) Inventors: William F. McKay, Memphis, TN (US); John Myers Zanella, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 70 days.

This patent is subject to a terminal disclaimer.

(21) Appl. No.: 13/110,618

(22) Filed: May 18, 2011

(65) Prior Publication Data

US 2011/0217382 A1    Sep. 8, 2011

Related U.S. Application Data

(63) Continuation of application No. 12/105,809, filed on Apr. 18, 2008, now Pat. No. 7,993,666.

(51) Int. Cl.
*A61K 31/351* (2006.01)
*A61K 9/14* (2006.01)
*A61P 25/04* (2006.01)

(52) U.S. Cl.
USPC .................. 424/424; 424/489; 514/460

(58) Field of Classification Search
None
See application file for complete search history.

(56) References Cited

U.S. PATENT DOCUMENTS

| | | | |
|---|---|---|---|
| 6,046,187 A * | 4/2000 | Berde et al. | 514/180 |
| 7,368,126 B2 * | 5/2008 | Chen et al. | 424/426 |
| 2004/0229878 A1 | 11/2004 | DiMauro | |
| 2005/0025765 A1 | 2/2005 | DiMauro | |
| 2005/0026979 A1 * | 2/2005 | Ghazzi et al. | 514/381 |
| 2005/0038001 A1 | 2/2005 | Attawia | |
| 2006/0046961 A1 | 3/2006 | McKay et al. | |
| 2006/0253100 A1 * | 11/2006 | Burright et al. | 604/512 |
| 2007/0099868 A1 | 5/2007 | Harats et al. | |
| 2007/0265329 A1 * | 11/2007 | Devang et al. | 514/419 |
| 2008/0064841 A1 * | 3/2008 | Hafeli et al. | 528/9 |
| 2008/0317805 A1 | 12/2008 | McKay et al. | |
| 2009/0263453 A1 | 10/2009 | McKay et al. | |

FOREIGN PATENT DOCUMENTS

| | | | |
|---|---|---|---|
| WO | 2000034475 A1 | | 6/2000 |
| WO | WO 2000/034475 | * | 6/2000 |
| WO | 2008014066 A1 | | 1/2008 |

OTHER PUBLICATIONS

Santovena et al. in Biomaterials 25 (2004) 925-931.*
'Sensor One dynecm2 conversion table' in www.sensorone.co.uk/pressure-measurement-glossary/.*
Santovena at al. Biomaterials 25 (2004) 925-931.*
Inherent Viscosity in www.absortables.com/inherentviscosity.thm.*

* cited by examiner

*Primary Examiner* — Robert A Wax
*Assistant Examiner* — Danah Al-Awadi
(74) *Attorney, Agent, or Firm* — Sorell Lenna & Schmidt LLP

(57) ABSTRACT

Methods and compositions are provided for reducing, treating or preventing pain and/or inflammation in a patient in need of such treatment, the methods and compositions comprising administering a therapeutically effective amount of a statin or pharmaceutically acceptable salt thereof to a target tissue site beneath the skin.

20 Claims, 6 Drawing Sheets

METHODS AND COMPOSITIONS FOR TREATING PAIN COMPRISING A STATIN

CROSS REFERENCE TO RELATED APPLICATION

This application is a continuation of U.S. patent application Ser. No. 12/105,809, filed Apr. 18, 2008 now U.S. Pat. No. 7,993,666.

BACKGROUND

Pain can adversely affect patients in many different ways. It can keep the patient from being active, sleeping well, enjoying family and friends, and from eating. Pain can make the patient feel afraid or depressed and prevent full participation in general rehabilitation programs and may even slow recovery.

Proper pain control is of prime importance to anyone treating many different diseases or conditions. Proper pain relief imparts significant physiological and psychological benefits to the patient. Not only does effective pain relief mean a smoother more pleasant recovery (e.g., mood, sleep, quality of life, etc.) with earlier discharge from medical/surgical/outpatient facilities, but it may also reduce the onset of chronic pain syndromes (e.g., fibromyalgia, myalgia, etc.).

Pain serves the important biological function of signaling the presence of damage or disease within the body and is often accompanied by inflammation (redness, swelling, and/or burning). There are two categories of pain: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends. As contrasted to acute pain, in general, neuropathic pain serves no beneficial purpose. Neuropathic pain results when pain associated with an injury or infection continues in an area once the injury or infection has resolved.

There are many painful disease or conditions that require proper pain and/or inflammation control. Such diseases or conditions include rheumatoid arthritis, osteoarthritis, sciatica, carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, or the like.

One particularly painful disease is sciatica. Sciatica is a chronic disease that often can be very debilitating and may take a terrible toll on those with the disease as well as their families, friends and caregivers. Sciatica is a very painful disease associated with the sciatic nerve which runs from the lower part of the spinal cord (the lumbar region), down the back of the leg and to the foot. Sciatica generally begins with a herniated disc, which later leads to local immune system activation. The herniated disc also may damage the nerve root by pinching or compressing it, leading to additional immune system activation in the area.

Another particularly painful disease is spinal stenosis, where there is progressive constriction of the spinal canal and as it narrows, the nerve elements that reside within it become progressively more crowded. Eventually, the canal dimensions become sufficiently small-so as to significantly compress the nerve elements and produce pain, weakness, sensory changes, clumsiness and other manifestation of nervous system dysfunction. The disease causes lower back pain, lower extremity pain, lower extremity weakness, limitation of mobility and the high disability rates that often afflict the elderly.

Spondylolisthesis is another painful disease. Spondylolisthesis is a displacement disorder of the lumbar or cervical spine, in which one vertebral body is forwardly displaced over another vertebral body. Spondylolisthesis may be caused by a traumatic event or by degeneration of the spine. At times, the displacement disorder is accompanied by or caused by a fracture or partial collapse of one or more vertebrae or degeneration of a disc in the spine. Patients who suffer from such conditions can experience moderate to severe distortion of the thoracic skeletal structure, diminished ability to bear loads, loss of mobility, extreme and debilitating pain, and oftentimes suffer neurological deficits in nerve function.

Statins are a family of molecules sharing the capacity to competitively inhibit the hepatic enzyme 3-hydroxy-3-methylglutaryl coenzyme A (HMG-CoA) reductase. This enzyme catalyses the rate-limiting step in the L-mevalonate pathway for cholesterol synthesis. Oral statin use blocks cholesterol synthesis and is effective in treating hypercholesterolemia. In recent years, oral statins have been shown to reduce cardiovascular-related morbidity and mortality in patients with and without coronary disease.

To date, locally delivered statins have not been appreciated for pain and/or inflammation control. New statin compositions and methods are needed to prevent, treat or reduce pain and/or inflammation. Statin compositions and methods that reliably provide pain and/or inflammation control are needed.

SUMMARY

New statin compositions and methods are provided that effectively prevent, treat or reduce pain and/or inflammation in chronic conditions including rheumatoid arthritis, osteoarthritis, a spinal disc herniation (i.e., sciatica), carpal/tarsal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, spondilothesis, stenosis, discogenic back pain, and joint pain or the like. In various embodiments, statin compositions and methods are provided that have long acting anti-inflammatory effects over periods of one day to 6 months. In various embodiments, new statin compositions and methods are provided, which can easily allow accurate and precise implantation of a drug depot containing the statin with minimal physical and psychological trauma to a patient. One advantage of the statin compositions and methods is that the drug depot can now be easily delivered to the target tissue site (e.g., nerve root, dorsal root ganglion, focal sites of pain, abdomen, synovial joint, at or near the spinal column, etc.) and provide pain and/or inflammation relief over an extended period of time.

In one embodiment, a method is provided for treating or preventing spondylothesis, stenosis, or sciatic pain and/or inflammation in a patient in need of such treatment, the method comprising locally administering a therapeutically effective amount of a statin or pharmaceutically acceptable salt thereof at or near a target tissue site beneath the skin of the patient to treat or prevent sciatic pain and/or inflammation.

In another embodiment, a method is provided for reducing spondylothesis, stenosis, or sciatic pain and/or inflammation in a patient in need of such treatment, the method comprising locally administering a therapeutically effective amount of a statin or pharmaceutically acceptable salt thereof at or near a target tissue site beneath the skin of the patient.

In one exemplary embodiment, an implantable drug depot is provided useful for reducing, preventing or treating pain and/or inflammation in a patient in need of such treatment, the implantable drug depot comprising a therapeutically effective amount of a statin or pharmaceutically acceptable salt thereof, the depot being implantable at a site beneath the skin to reduce, prevent or treat pain and/or inflammation, wherein the drug depot is capable of releasing an effective amount of a statin or pharmaceutically acceptable salt thereof over a period of at least one day.

In another exemplary embodiment, a method of making an implantable drug depot is provided, the method comprising combining a biocompatible polymer and a therapeutically effective amount of a statin or pharmaceutically acceptable salt thereof and forming the implantable drug depot from the combination.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
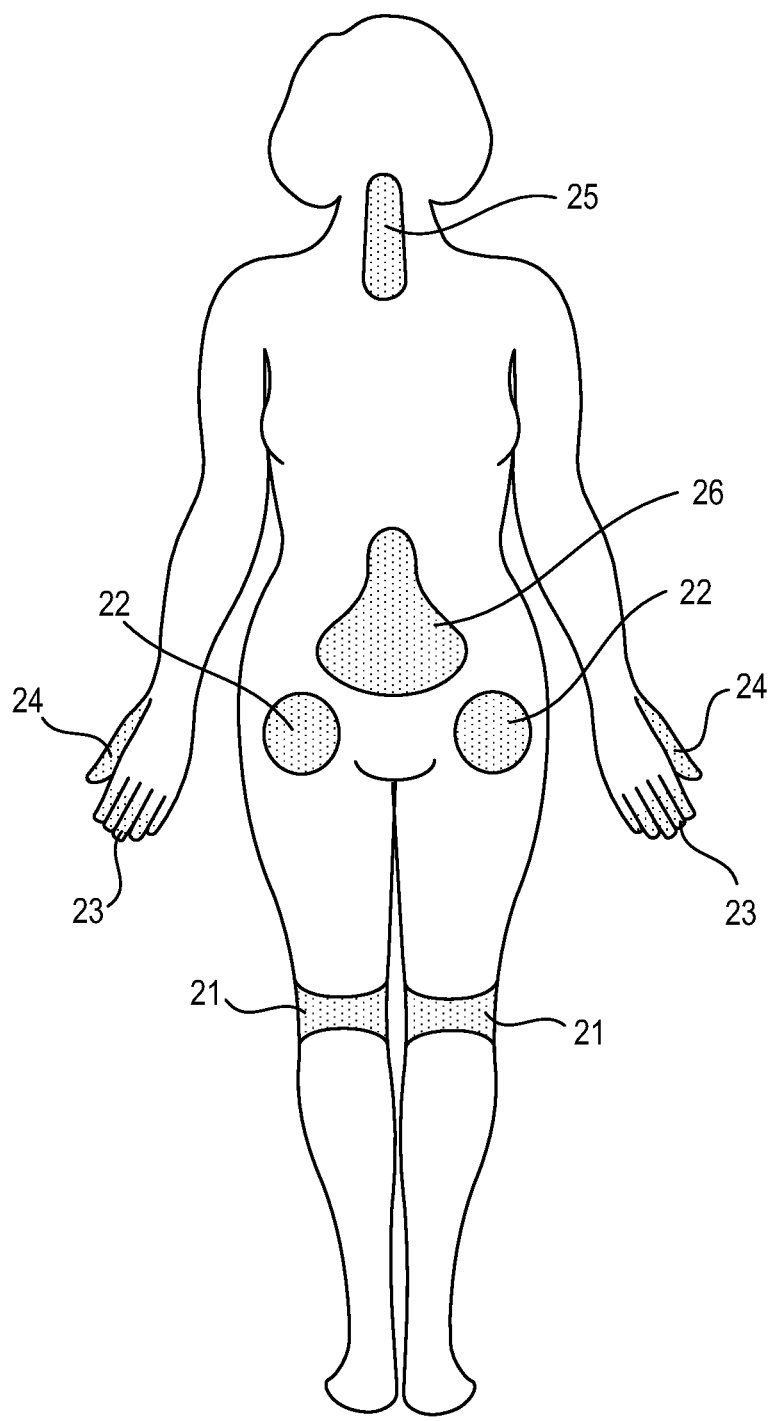
FIG. 1 illustrates a number of common locations within a patient where the parenteral statin formulation may be locally administered (e.g., injection, infusion, depot, etc.) to the target tissue site to treat pain and/or inflammation.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under any one heading may be used in conjunction with embodiments under any other heading.

New statin compositions and methods are provided that effectively prevent, treat or reduce pain and/or inflammation (e.g., acute pain, neuropathic pain, spondilothesis, stenosis, sciatica, radicular pain, etc.). In various embodiments, statin compositions and methods are provided that have long acting anti-inflammatory effects over periods of one day to 6 months. In various embodiments, new statin compositions and methods are provided, which can easily allow accurate and precise implantation of a drug depot containing the statin with minimal physical and psychological trauma to a patient. One advantage of the statin compositions and methods is that the drug depot can now be easily delivered to the target tissue site (e.g., nerve root, dorsal root ganglion, focal sites of pain, abdomen, synovial joint, at or near the spinal column, etc.) and provide pain and/or inflammation relief for one day to 6 months.

In one embodiment, a method of inhibiting, treating or preventing sciatic pain and/or inflammation in a patient is provided, the method comprising locally administering a therapeutically effective amount of a statin or pharmaceutically acceptable salt thereof at or near a target tissue site beneath the skin of the patient.

Statins

Statins include one or more compound(s) sharing the capacity to competitively inhibit the hepatic enzyme 3-hydroxy-3-methylglutaryl coenzyme A (HMG-CoA) reductase. This enzyme catalyses the rate-limiting step in the L-mevalonate pathway which is an early and rate-limiting step in the biosynthesis of cholesterol. Consequently, statins block cholesterol synthesis and are effective in treating hypercholesterolemia and may reduce cardiovascular-related morbidity and mortality in patients with and without coronary disease.

Compounds that inhibit the activity of HMG CoA reductase can be readily identified by using assays well known in the art; see, as examples, the assays described or cited in U.S. Pat. No. 4,231,938 at column 6, and in International Patent Publication WO 84/02131 at pp. 30-33.

A "therapeutically effective amount" or "effective amount" is such that when administered, the drug results in alteration of the biological activity, such as, for example, inhibition of inflammation, reduction or alleviation of pain, improvement in the condition, etc. It will be understood that the dosage administered to a patient can be as a single dose or multiple doses, continuous doses (e.g., continuous infusion) or depot or multiple depots depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. For example, lower daily doses of the statin may be needed when there is concurrent treatment with an opioid (e.g., morphine), alternatively, the patient may require higher doses of a statin as the dosage of the opioid (e.g., morphine) is reduced or eliminated.

In various embodiments, because the statin is locally administered, therapeutically effective doses may be less than doses used for elevated blood/plasma cholesterol, lipids and/or triglycerides. In turn, side effects, such as for example, liver transaminase elevations, hepatitis, liver failure, myopathy, rhabdomyolysis and resulting renal failure, proteinuria, and/or general malaise may be reduced or eliminated.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publ. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In various embodiments, natural products such as, for example, red yeast rice; Zhitai, Cholestin or Hypocol, and Xuezhikang contain statin compounds that act as HMG CoA reductase inhibitors.

Lovastatin is a statin that may be obtained from various manufacturers in various forms (e.g., injection, powder, etc.). For example, lovastatin may be obtained from Merck as Mevacor® (see U.S. Pat. No. 4,231,938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of atorvastin include lithium, calcium, hemicalcium, sodium, potassium, magnesium, aluminum, ferrous or ferric salts thereof or a combination thereof.

In various embodiments, the therapeutically effective amount of lovastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of lovastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day or from 40 ng/hr or 0.4 mcg/hr or from 6.9 mcg/kg/day to 0.68 mg/kg/day.

Atorvastatin is a statin that may be obtained from various manufacturers in various forms (e.g., injection, powder, etc.). For example, atorvastatin may be obtained from Pfizer as Lipitor® (see U.S. Pat. No. 5,273,995, the entire disclosure is herein incorporated by reference). The pharmaceutically acceptable salts of atorvastatin include one or more compounds that generally can be derived by dissolving the free acid or the lactone; for example, the lactone, in aqueous or aqueous alcohol solvent or other suitable solvents with an appropriate base and isolating the salt by evaporating the solution or by reacting the free acid or lactone.

Suitable pharmaceutically acceptable salts of atorvastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of atorvastin include lithium, calcium, hemicalcium, magnesium, zinc, sodium, potassium, magnesium, aluminum, ferrous or ferric salts thereof or a combination thereof.

In various embodiments, the therapeutically effective amount of atorvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of atorvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Simvastatin is a statin that may be obtained from various manufacturers in various forms (e.g., injection, powder, etc.). For example, simvastatin may be obtained from Merck as Zocor® (see U.S. Pat. No. 4,444,784, the entire disclosure is herein incorporated by reference). The pharmaceutically acceptable salts of simvastatin include those formed from cations such as, for example, sodium, potassium, aluminum, calcium, lithium, magnesium, zinc or tetramethylammonium as well as those salts formed from amines such as, for example, ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, or tris(hydroxymethyl)aminomethane or a combination thereof.

In various embodiments, the therapeutically effective amount of simvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of simvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Pravastatin is a statin that may be obtained from various manufacturers in various forms (e.g., injection, powder, liquid, etc.). For example, pravastatin may be obtained from Bristol-Myers Squibb as Pravachol® (see U.S. Pat. No. 4,346,227, the entire disclosure is herein incorporated by reference). Suitable pharmaceutically acceptable salts of pravastatin include one or more compounds derived from bases or acids, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide, hydroxy-carboxylic acids or organic amines such as N-methylglucamine, choline, arginine or the like or esters of the hydroxy-carboxylic acids of pravastatin or a combination thereof. Suitable pharmaceutically acceptable salts of pravastatin include lithium, calcium, hemicalcium, magnesium, zinc, sodium, potassium, magnesium, aluminum, ferrous or ferric salts thereof a combination thereof.

In various embodiments, the therapeutically effective amount of pravastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of pravastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Cerivastatin (also known as rivastatin) is a statin that may be obtained from various manufacturers in various forms (e.g., injection, powder, liquid, etc.). For example, cerivastatin may be obtained from Bayer AG as Baychol® (see U.S. Pat. No. 5,502,199, the entire disclosure is herein incorporated by reference). Suitable pharmaceutically acceptable salts of cerivastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of cerivastatin include lithium, calcium, hemicalcium, magnesium, zinc, sodium, potassium, magnesium, aluminum, ferrous or ferric salts thereof or a combination thereof.

In various embodiments, the therapeutically effective amount of cerivastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of cerivastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Fluvastatin is a statin that may be obtained from various manufacturers in various forms (e.g., injection, powder, liquid, etc.). For example, fluvastatin may be obtained from Novartis Pharmaceuticals as Lescol® (see U.S. Pat. No. 5,354,772, the entire disclosure is herein incorporated by reference). Some examples, of pharmaceutically acceptable salts include, for example, pharmaceutically acceptable salts of phosphoric acid such as tribasic calcium phosphate or inorganic carbonate and bicarbonate salts, e.g., sodium carbonate, sodium bicarbonate, calcium carbonate, or mixtures thereof. Suitable pharmaceutically acceptable salts of fluvastatin include lithium, calcium, hemicalcium, magnesium, zinc, sodium, potassium, magnesium, aluminum, ferrous or ferric salts thereof or a combination thereof.

In various embodiments, the therapeutically effective amount of fluvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of fluvastatin per day. For example, the dose may be 0.1 to 10 mg/kg of body weight.

Rosuvastatin is a statin that may be obtained from various manufacturers in various forms (e.g., injection, powder, liquid, etc.). For example, rosuvastatin may be obtained from AstraZeneca as Crestor® (See U.S. Pat. Nos. 6,316,460, 6,858,618, and RE37314, the entire disclosures are herein incorporated by reference). Suitable pharmaceutically acceptable salts of rosuvastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of rosuvastatin include lithium, calcium, hemicalcium, tribasic calcium phosphate, magnesium, zinc, sodium, potassium, magnesium, aluminum, ferrous or ferric salts thereof or a combination thereof.

In various embodiments, the therapeutically effective amount of rosuvastatin comprises from about 0.1 mg to about 2000 mg, for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of rosuvastatin per day. In various embodiments, dosages of from 10 to 500 mg per day may be given, which for a normal human adult of approximately 70 kg is a dosage of from 0.14 to 7.1 mg/kg of body weight per day. In various embodiments, the dosage may be, for example from 0.1 to 1.0 mg/kg per day or from about 0.3 mg/kg/day to 3 mg/kg/day.

Pitavastatin is a statin that may be obtained from various manufacturers in various forms (e.g., injection, powder, liquid, etc.). Suitable pharmaceutically acceptable salts of pitavastatin include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of pitavastatin include lithium, calcium, hemicalcium, tribasic calcium phosphate, magnesium, zinc, sodium, potassium, magnesium, aluminum, ferrous or ferric salts thereof or a combination thereof.

In various embodiments, the dosage of pitavastatin can be between 1 to 100 mg/day for example 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of pitavastatin. In various embodiments, pitavastatin may be given at a dose of, for example, from 0.1 to 1.0 mg/kg per day or from about 0.3 mg/kg/day to 3 mg/kg/day.

Eptastatin, velostatin, fluindostatin, or dalvastain are statins that may be obtained from various manufacturers in various forms (e.g., injection, powder, liquid, etc.). Suitable pharmaceutically acceptable salts of eptastatin, velostatin, fluindostatin, or dalvastain include one or more compounds derived from bases, such as for example, sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of eptastatin, velostatin, fluindostatin, or dalvastain include lithium, calcium, hemicalcium, tribasic calcium phosphate, magnesium, zinc, sodium, potassium, magnesium, aluminum, ferrous or ferric salts thereof or a combination thereof.

In various embodiments, the dosage of eptastatin, velostatin, fluindostatin, or dalvastain can be between 1 to 100 mg/day for example 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, or 100 mg of eptastatin velostatin, fluindostatin, or dalvastain. In various embodiments, eptastatin may be given at a dose of, for example, from 0.1 to 1.0 mg/kg per day or from about 0.3 mg/kg/day to 3 mg/kg/day.

The statin can be administered in parenteral formulations. The term "parenteral" as used herein refers to modes of administration, which bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intraarticular injection or combinations thereof.

Statin formulations for parenteral use can comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles include water, ethanol, polyols (such as glycerol, propylene glycol, polyethylene glycol, or the like), carboxymethylcellulose or suitable mixtures thereof or vegetable oils (such as olive oil), or injectable organic esters such as ethyl oleate, or agents that delay absorption (e.g., liposomes, microemulsions, etc.). In various embodiments, the parenteral formulation may be preservative free. In various embodiments, the parenteral formulation may contain adjuvants such as preservatives (e.g., paraben, chlorobutanol, BHT, benzalkonium chloride, etc.), wetting agents, emulsifying agents, and/or dispersing agents. The parenteral formulations may include isotonic agents such as sugars, sodium chloride, or the like.

In one embodiment, one or more statins can be parenterally administered locally by insertion of a catheter at or near a target site (e.g., nerve root, dorsal root ganglion, focal sites of pain, abdomen, synovial joint, at or near the spinal column, etc.), the catheter having a proximal end and a distal end, the distal end having an opening to deliver a pharmaceutical in situ, the proximal end being fluidly connected, in various embodiments, to a pharmaceutical delivery pump. In various embodiments, a catheter or syringe is optionally operably connected to a pharmaceutical delivery pump. It is understood that pumps can be internal or external as appropriate.

In various embodiments, the parenteral administration may additionally include, for example, an infusion pump that administers a pharmaceutical composition (e.g., statin) through a catheter near the spine or one or more inflamed joints, an implantable mini-pump that can be inserted at or near the target site, an implantable controlled release device or sustained release delivery system that can release a certain amount of the statin per hour or in intermittent bolus doses. One example of a suitable pump for use is the SynchroMed® (Medtronic, Minneapolis, Minn.) pump. This pump has three sealed chambers. One contains an electronic module and battery. The second contains a peristaltic pump and drug reservoir. The third contains an inert gas, which provides the pressure needed to force the pharmaceutical composition into the peristaltic pump. To fill the pump, the pharmaceutical composition is injected through the reservoir fill port to the expandable reservoir. The inert gas creates pressure on the reservoir, and the pressure forces the pharmaceutical composition through a filter and into the pump chamber. The pharmaceutical composition is then pumped out of the device from the pump chamber and into the catheter, which will direct it for deposit at the target site. The rate of delivery of pharmaceutical composition is controlled by a microprocessor. This allows the pump to be used to deliver similar or different amounts of pharmaceutical composition continuously, at specific times, or at set intervals between deliveries.

Potential drug delivery devices suitable for adaptation for the methods described herein include but are not limited to those described, for example, in U.S. Pat. No. 6,551,290 (assigned to Medtronic, the entire disclosure is herein incorporated by reference), which describes a medical catheter for target specific drug delivery; U.S. Pat. No. 6,571,125 (assigned to Medtronic, the entire disclosure is herein incorporated by reference), which describes an implantable medical device for controllably releasing a biologically active agent; U.S. Pat. No. 6,594,880 (assigned to Medtronic, the entire disclosure is herein incorporated by reference), which describes an intraparenchymal infusion catheter system for delivering therapeutic agents to selected sites in an organism; and U.S. Pat. No. 5,752,930 (assigned to Medtronic, the entire disclosure is herein incorporated by reference), which describes an implantable catheter for infusing equal volumes of agents to spaced sites. In various embodiments, pumps may be adapted with a pre-programmable implantable apparatus with a feedback regulated delivery, a micro-reservoir osmotic release system for controlled release of chemicals, small, light-weight devices for delivering liquid medication, implantable microminiature infusion devices, implantable ceramic valve pump assemblies, or implantable infusion pumps with a collapsible fluid chamber. Alzet® osmotic pumps (Durect Corporation, Cupertino, Calif.) are also available in a variety of sizes, pumping rates, and durations suitable for use in the described methods.

In various embodiments, the statin is locally delivered by a targeted delivery system comprising an interbody pump and a catheter, the catheter having a proximal end and a distal end, the distal end having an opening to deliver a pharmaceutical composition in situ, and a proximal end of the catheter being fluidly connected to the interbody pump. It will be appreciated that a localized delivery device, such as a pump or the like, may be used to deliver the statin to the targeted tissue site. Examples of localized delivery systems are presented in co-pending U.S. patent application Ser. No. 11/091,348, which is incorporated herein by reference.

In various embodiments, the statin is contained in a drug depot. A drug depot comprises a physical structure to facilitate implantation and retention in a desired site (e.g., a synovial joint, a disc space, a spinal canal, abdominal area, a tissue of the patient, etc.). The drug depot also comprises the drug. The term "drug" as used herein is generally meant to refer to any substance that alters the physiology of a the patient. The term "drug" may be used interchangeably herein with the terms "therapeutic agent", "therapeutically effective amount", and "active pharmaceutical ingredient" or "API". It will be understood that a "drug" formulation may include more than one therapeutic agent, wherein exemplary combinations of therapeutic agents include a combination of two or more drugs. The drug depot provides a concentration gradient of the therapeutic agent for delivery to the site. In various embodiments, the drug depot provides an optimal drug concentration gradient of the therapeutic agent at a distance of up to about 0.1 cm to about 5 cm from the implant site.

In various embodiments a therapeutically effective amount of a statin is provided to inhibit, treat and/or prevent pain or inflammation.

In addition to the statin, the drug depot may comprise one or more additional therapeutic agents. Examples of therapeutic agents include, those that are direct- and local-acting modulators of pro-inflammatory cytokines such as TNF-α and IL-1 including, but not limited to, soluble tumor necrosis factor α receptors, any pegylated soluble tumor necrosis factor α receptor, monoclonal or polyclonal antibodies or antibody fragments or combinations thereof. Examples of suitable therapeutic agents include receptor antagonists, molecules that compete with the receptor for binding to the target molecule, antisense polynucleotides, and inhibitors of transcription of the DNA encoding the target protein. Suitable examples include but are not limited to Adalimumab, Infliximab, Etanercept, Pegsunercept (PEG sTNF-R1), sTNF-R1, CDP-870, CDP-571, CNI-1493, RDP58, ISIS 104838, 1→3-β-D-glucans, Lenercept, PEG-sTNFRII Fc Mutein, D2E7, Afelimomab, and combinations thereof. In other embodiments, a therapeutic agent includes metalloprotease inhibitors, glutamate antagonists, glial cell-derived neurotropic factors (GDNF), B2 receptor antagonists, Substance P receptor (NK1) antagonists such as capsaicin and civamide, downstream regulatory element antagonistic modulator (DREAM), iNOS, inhibitors of tetrodotoxin (TTX)-resistant Na+-channel receptor subtypes PN3 and SNS2, inhibitors of interleukins such as IL-1, IL-6 and IL-8, and anti-inflammatory cytokines, TNF binding protein, onercept (r-hTBP-1), recombinant adeno-associated viral (rAAV) vectors encoding inhibitors, enhancers, potentiators, or neutralizers, antibodies, including but not limited to naturally occurring or synthetic, double-chain, single-chain, or fragments thereof. For example, suitable therapeutic agents include molecules that are based on single chain antibodies called Nanobodies™ (Ablynx, Ghent Belgium), which are defined as the smallest functional fragment of a naturally occurring, single-domain antibody. Alternatively, therapeutic agents include, agents that effect kinases and/or inhibit cell signaling mitogen-activated protein kinases (MAPK), p38 MAPK, Src or protein tyrosine kinase (PTK).

Therapeutic agents include, kinase inhibitors such as, for example, Gleevec, Herceptin, Iressa, imatinib (STI571), herbimycin A, tyrphostin 47, erbstatin, genistein, staurosporine, PD98059, SB203580, CNI-1493, VX-50/702 (Vertex/Kissei), SB203580, BIRB 796 (Boehringer Ingelheim), Glaxo P38 MAP Kinase inhibitor, RWJ67657 (J&J), UO126, Gd, SCIO-469 (Scios), RO3201195 (Roche), Semipimod (Cytokine PharmaSciences), or derivatives thereof.

Therapeutic agents, in various embodiments, block the transcription or translation of TNF-α or other proteins in the inflammation cascade. Suitable therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents include IL-1 inhibitors, such Kineret® (anakinra) which is a recombinant, non-glycosylated form of the human inerleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), bone morphogenetic protein (BMP) type 2 and BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), for example, may also be useful as therapeutic agents for reducing inflammation. It is contemplated that where desirable a pegylated form of the above may be used. Examples of other therapeutic agents include NF kappa B inhibitors such as glucocorticoids, clonidine; antioxidants, such as dilhiocarbamate, and other compounds, such as, for example, sulfasalazine.

Specific examples of therapeutic agents suitable for use include, but are not limited to an anti-inflammatory agent, analgesic agent, or osteoinductive growth factor or a combination thereof. Anti-inflammatory agents include, but are not limited to, salicylates, diflunisal, sulfasalazine, indomethacin, ibuprofen, naproxen, tolmetin, ketorolac, diclofenac, ketoprofen, fenamates (mefenamic acid, meclofenamic acid), enolic acids (piroxicam, meloxicam), nabumetone, celecoxib, etodolac, nimesulide, apazone, gold, sulindac or tepoxalin; antioxidants, such as dithiocarbamate, and other compounds such as sulfasalazine [2-hydroxy-5-[-4-[C2-pyridinylamino)sulfonyl]azo]benzoic acid], steroids, such as fluocinolone, cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine or a combination thereof.

Analgesics also include agents with analgesic properties, such as for example, amitriptyline, carbamazepine, gabapentin, pregabalin, clonidine, or a combination thereof.

The depot may contain a muscle relaxant. Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The depot comprises the therapeutic agent or agents and may also contain other non-active ingredients. It has a multifunctional purpose including the carrying, stabilizing and controlling the release of the therapeutic agent(s). The controlled release process, for example, may be by a solution-diffusion mechanism or it may be governed by an erosion-controlled process. Typically, the depot will be a solid or semi-solid formulation comprised of a biocompatible material, which can be biodegradable. The term "solid" is intended to mean a rigid material, while, "semi-solid" is intended to mean a material that has some degree of flexibility, thereby allowing the depot to bend and conform to the surrounding tissue requirements.

In various embodiments, the depot material will be durable within the tissue site for a period of time equal to (for biodegradable components) or greater than (for non-biodegradable components) the planned period of drug delivery. For example, the depot material may have a melting point or glass transition temperature close to or higher than body temperature, but lower then the decomposition or degradation temperature of the therapeutic agent. However, the pre-determined erosion of the depot material can also be used to provide for slow release of the loaded therapeutic agent(s).

In various embodiments, the drug depot may be designed to release the statin when certain trigger points are reached (e.g., temperature, pH, etc.) after implantation in vivo. For example, the drug depot may comprise polymers that will release more drug as the body temperature reaches greater than, for example, 102° F., particularly if the drug possesses antipyretic properties. In various embodiments, depending on the site of implantation, the drug depot may release more or less drug as a certain pH is reached. For example, the drug depot may be designed to release the drug as the bodily fluid having a certain pH contact the drug depot (e.g., CSF having a pH of about 7.35 to about 7.70, synovial fluid having a pH of about 7.29 to about 7.45; urine having a pH of about 4.6 to about 8.0, pleural fluids having a pH of about 7.2 to about 7.4, blood having a pH of about 7.35 to about 7.45, etc.)

In various embodiments, the depot may have a high drug loading, such that the statin and/or other therapeutic agent comprises about 5-99 wt % of the depot, or 30-95 wt % of the depot, or 50-95 wt % of the depot. In various embodiments, the amount of a statin and/or other therapeutic agent are present in the depot in a range from about 0.1% to about 40% by weight of the depot (including 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, and ranges between any two of these points, for instance, 0.1-10%, 10-20% and 20-30%, etc.). In various embodiments, a statin can be used in a load range of 2-20%.

In various embodiments, the drug depot may release 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 105 mg, 110 mg, 115 mg, 120 mg, 125 mg, 130 mg, 135 mg, or 140 mg of a statin per day for a total of 1 day to 6 months. In various embodiments, the drug depot may release 0.1 mg to 10 mg of the statin per hour for a total of 1 day to 6 months to reduce, treat or prevent pain. In various embodiments, the drug depot releases 5%, 10%, 15%, 20%, 25%, 30%, 40%, 50%, 60%, 70%, 80%, 90%, 95%, or 99% of the statin over a period of 1 day to 6 months after the drug depot is administered to the target tissue site. The drug depot may have a "release rate profile" that refers to the percentage of active ingredient that is released over fixed units of time, e.g., mg/hr, mg/day, 10% per day for 1 day to 6 months, etc. As persons of ordinary skill know a release rate profile may be but need not be linear.

In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof. Exemplary non-biodegradable material include, for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyetherurethane, polycarbonate-urethane and silicone polyether-urethane. Typically, the non-degradable drug depots may need to be removed. Typically, these types of drug depots may need to be removed.

In some instances, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

A "depot" includes but is not limited to capsules, microspheres, microparticles, microcapsules, microfibers particles, nanospheres, nanoparticles, coating, matrices, wafers, pills, pellets, emulsions, liposomes, micelles, gels, or other pharmaceutical delivery compositions. Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. The depot may also comprise a drug pump.

The term "biodegradable" includes that all or parts of the drug depot will degrade over time by the action of enzymes, by hydrolytic action and/or by other similar mechanisms in the human body. In various embodiments, "biodegradable" includes that depot (e.g., microparticle, microsphere, gel, etc.) can break down or degrade within the body to non-toxic components after or while a therapeutic agent has been or is being released. By "bioerodible" it is meant that the depot and/or gel will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

In various embodiments, the depot may comprise a biocompatible, bioabsorbable, and/or a biodegradable biopolymer that may provide immediate release, sustained release or controlled release of the drug. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG), PEG 200, PEG 300, PEG 400, PEG 500, PEG 550, PEG 600, PEG 700, PEG 800, PEG 900, PEG 1000, PEG 1450, PEG 3350, PEG 4500, PEG 8000, conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) hydroxypropyl cellulose, hydroxypropyl methylcellulose, hydroxyethyl methylcellulose, carboxymethylcellulose or salts thereof, Carbopol, poly(hydroxyethylmethacrylate), poly(methoxyethylmethacrylate), poly (methoxyethoxy-ethylmethacrylate), polymethylmethacrylate (PMMA), methylmethacrylate (MMA), gelatin, polyvinyl alcohols, propylene glycol, or combinations thereof.

In various embodiments, when the drug depot comprises a polymer, it is employed at about 10 wt % to about 99 wt % or about 30 wt % to about 60 wt % based on the weight of the drug depot.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed in the spinal area or joint area, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a sphere, a cylinder such as a rod or fiber, a flat surface such as a disc, film, ribbon or sheet, or the like. Flexibility may be a consideration so as to facilitate placement of the drug depot. In various embodiments, the drug depot can be different sizes, for example, the drug depot may be a length of from about 0.01 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

Radiographic markers can be included on the drug depot to permit the user to accurately position the depot into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles. Where present, the radiographic marker is typically present in an amount of from about 10% to about 40% (including 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% and 40%, as well as ranges between any two of these values, e.g., 10-15%, 15-20%, 20-25%, 25-30%, 30-35%, 35-40%, and so forth, with 15-30% being more typical, even more typically 20-25%). In various embodiments, the radiographic marker could be a spherical shape or a ring around the depot.

In one exemplary embodiment, a drug depot for delivering a therapeutic agent to a target tissue site beneath the skin of a patient is provided, the drug depot comprising an effective amount of a statin, wherein the target tissue site comprises at least one muscle, ligament, tendon, cartilage, spinal disc, spinal foraminal space near the spinal nerve root, facet or synovial joint, or spinal canal.

In various embodiments, the drug depot comprises a gel, which includes a substance having a gelatinous, jelly-like, or colloidal properties at room temperature. The gel, in various embodiments, may have the statin and optionally one or more additional therapeutic agents dispersed throughout it or suspended within the gel. The dispersal of the therapeutic agent may be even throughout the gel. Alternatively, the concentration of the therapeutic agent may vary throughout it. As the biodegradable material of the gel or drug depot degrades at the site, the therapeutic agent is released.

When the drug depot is a gel, in contrast to a sprayable gel that typically employs a low viscosity polymer, a gel with a higher viscosity may be desirable for other applications, for example, a gel having a putty-like consistency may be more preferable for bone regeneration applications.

In another exemplary embodiment, a viscous gel is provided that is loaded with one or more drug depots (e.g., microspheres loaded with a therapeutic agent), wherein the viscous gel is positioned into a synovial joint, disc space, a spinal canal, or a soft tissue surrounding the spinal canal of a subject. The gel can also be used, in various embodiments, to seal or repair tissue. In yet another exemplary embodiment, the gel is injectable, and/or an adherent gel that solidifies upon contact with tissue. For example, the gel may be administered as a liquid that gels in situ at the target tissue site. In various embodiments, the gel can comprise a two part system where a liquid is administered and a gelling agent is added subsequently to cause the liquid to gel or harden.

In various embodiments, the drug depot is loaded with a statin and optionally one or more additional therapeutic agents, and delivered to the desired target tissue site (e.g., surgical wound site, inflamed tissue, degenerative tissue, etc.) and, in various embodiments, the drug depot may be held in place by a suture, barb, staple, adhesive gel, etc. which prevents the drug depot from being removed from that site by the venous systemic circulation or otherwise dispersed too widely, which reduces the desired therapeutic effect. For example, after hours or days, the drug depot may degrade, thereby allowing the drug depots (e.g., microspheres) to begin releasing the therapeutic agent. The microspheres do not begin releasing the agent until they are released from the drug depot. So, the microspheres may be formed from an insoluble or inert substances, but soluble or active once it comes into contact with the target tissue site. Likewise, the drug depot may comprise a substance that dissolves or disperses within the tissue. As the drug depot begins to dissolve within hours to days, the drug depots (e.g., microspheres) are exposed to body fluids and begin releasing their contents. The drug depot can be formulated to optimize exposure time of the drug depot and release of the therapeutic agent from the drug depot. In various embodiments, the drug depot (e.g., gel) is flowable and can be injected, sprayed, instilled, and/or dispensed to, on or in the target tissue site. "Flowable" means that the gel formulation is easy to manipulate and may be brushed, sprayed, dripped, injected, shaped and/or molded at or near the target tissue site as it coagulates. "Flowable" includes formulations with a low viscosity or water-like consistency to those with a high viscosity, such as a paste-like material. In various embodiments, the flowability of the formulation allows it to conform to irregularities, crevices, cracks, and/or voids in the tissue site. For example, in various embodiments, the gel may be used to fill one or more voids in an osteolytic lesion.

In various embodiments, the drug depot comprises poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pregelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG (poly(d,l-lactide-co-glycolide), PLA-PLGA, poloxamer 407, PEG-PLGA-PEG triblock copolymers, SAIB (sucrose acetate isobutyrate) or combinations thereof. These one or more components allow the therapeutic agent to be released from the drug depot in a controlled and/or sustained manner. For example, the drug depot containing the therapeutic agent and a polymer matrix can be injected at the target tissue site and the polymer matrix breaks down over time (e.g., hours, days) within the target tissue site releasing a statin and optionally additional therapeutic agents. Thus the administration of the drug depot can be localized and occur over a period of time (e.g., at least one day to about 2, 3, 4, 5, 6, 7, 8, 9, 10 days or months). In some embodiments, the therapeutically effective dosage amount (e.g., statin) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 150 days, or 3 days to 6 months or 1 year.

The terms "sustained release" (e.g., extended release or controlled release) are used herein to refer to one or more therapeutic agent(s) that is introduced into the body of a human or other mammal and continuously releases a stream of one or more therapeutic agents over a predetermined time period and at a therapeutic level sufficient to achieve a desired therapeutic effect throughout the predetermined time period. Reference to a continuous release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s).

In various embodiments, the drug depot can be designed to cause an initial burst dose of therapeutic agent within the first 24 hours after implantation. "Initial burst" or "burst effect" or "bolus dose" refers to the release of therapeutic agent from the drug depot during the first 24 hours after the drug depot comes in contact with an aqueous fluid (e.g., synovial fluid, cerebral spinal fluid, etc.). In various embodiments, the drug depot is designed to avoid this initial burst effect.

In various embodiments, the drug depot contains one or more different release layer(s) that releases a bolus dose of a statin or pharmaceutically acceptable salt thereof (e.g., 5 mg to 60 mg at a target site beneath the skin) and one or more sustain release layer(s) that releases an effective amount of a statin or pharmaceutically acceptable salt thereof over a period of one day to 6 months. In various embodiments, the one or more immediate release layer(s) comprise PLGA, which degrades faster and than the one or more sustain release layer(s), which comprises PLA, which degrades at a slower rate than the PLGA.

In various embodiments, when the drug depot comprises a gel, the gel may have a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1\times10^4$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, the gel may be an adherent gel, which comprises a therapeutic agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject or spray the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or adhere to the target tissue.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in bone).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example when applying the formulation via spray.

In various embodiments, the molecular weight of the gel can be varied by many methods known in the art. The choice of method to vary molecular weight is typically determined by the composition of the gel (e.g., polymer, versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), crosslinking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature, which allows it to be sprayed at or near the target site.

In various embodiments, the drug depot may comprise material to enhance viscosity and control the release of the drug such material may include, for example, hydroxypropyl cellulose, hydroxypropyl methylcellulose, hydroxyethyl methylcellulose, carboxymethylcellulose and salts thereof, Carbopol, poly(hydroxyethylmethacrylate), poly(methoxyethylmethacrylate), poly(methoxyethoxy-ethylmethacrylate), polymethyl-methacrylate (PMMA), methylmethacrylate (MMA), gelatin, polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. For example, in various embodiments, the drug depot comprises from about 2.5% to 60% by weight of a statin, which is sprayed with from about 40% to 60% by weight PLGA, 5% to 40% by weight of PEG550.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

When there are other active ingredients, surfactants, excipients or other ingredients or combinations thereof in the formulation, in some embodiments, these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %. Exemplary excipients include but are not limited to mPEG, D-Sorbital, maltodextran, cyclodextrin and combinations thereof.

The drug depot release profile can also be controlled, among other things, by controlling the particle size distribution of the components of the drug depot. In various embodiments, the particle size distribution of the components of the drug depot (e.g., statin, gel, etc.) may be in the range of from about 10 μM to 100 μM so that the drug depot can easily be delivered to or at or near the target site by injection, spraying, instilling, etc.

In some embodiments, at least 75% of the particles have a size from about 1 micrometer to about 250 micrometers. In some embodiments, at least 85% of the particles have a size from about 5 micrometer to about 100 micrometers. In some embodiments, at least 95% of the particles have a size from about 10 micrometer to about 30 micrometers. In some embodiments, all of the particles have a size from about 10 micrometer to about 250 micrometers.

As persons of ordinary skill in the art are aware, implantable depot compositions having a blend of polymers with different end groups are used the resulting formulation will be able to regulate the duration of delivery. For example, one may use polymers with acid (e.g., carboxylic acid) and ester end groups (e.g., methyl of ethyl ester end groups).

Additionally, by varying the comonomer ratio of the various monomers that form a polymer (e.g., the L/G (lactic acid/glycolic acid) or G/CL (glycolic acid/polycaprolactone) ratio for a given polymer) there will be a resulting depot composition having a regulated burst index and duration of delivery. For example, a depot composition having a polymer with a L/G ratio of 50:50 may have a short duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery. Thus, among other things, depot compositions having a blend of polymers having different molecular weights, end groups and comonomer ratios can be used to create a depot formulation having a lower burst index and a regulated duration of delivery.

In various embodiments, the drug depot may comprise a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing since they are more likely to be biodegradable and biocompatible for in vivo applications. Suitable hydrogels include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agent into the drug depot, microspheres may be dispersed within the drug depot, the microspheres loaded with the therapeutic agent. In one embodiment, the microspheres provide for a sustained release of the therapeutic agent. In yet another embodiment, the drug depot, which is biodegradable, prevents the microspheres from releasing the therapeutic agent; the microspheres thus do not release the therapeutic agent until they have been released from the depot. For example, a drug depot may be deployed around a target tissue site (e.g., DRG, synovial joint, etc.). Dispersed within the drug depot are a plurality of microspheres that encapsulate the desired therapeutic agent. Certain of these microspheres degrade once released from the drug depot, thus releasing the therapeutic agent.

Microspheres, much like a fluid, may disperse relatively quickly, depending upon the surrounding tissue type, and hence disperse the therapeutic agent. In some situations, this may be desirable; in others, it may be more desirable to keep the therapeutic agent tightly constrained to a well-defined target site.

Cannula or Needle

It will be appreciated by those with skill in the art that the depot can be administered to the target site using a cannula or needle that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. For example, the width of the epidural space is only about 3-5 mm for the thoracic region and about 5-7 mm for the lumbar region. Thus, the needle or cannula, in various embodiments, can be designed for these specific areas. In various embodiments, the cannula or needle may be inserted using a transforaminal approach in the spinal foramen space, for example, along an inflamed nerve root and the drug depot implanted at this site for treating the condition. Typically, the transforaminal approach involves approaching the intervertebral space through the intervertebral foramina.

Some examples of lengths of the cannula or needle may include, but are not limited to, from about 50 to 150 mm in length, for example, about 65 mm for epidural pediatric use, about 85 mm for a standard adult and about 110 mm for an obese adult patient. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 22 gauge. In various embodiments the gauge of the needle or cannula is about 18 to about 22 gauge.

In various embodiments, like the drug depot, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

The drug depot, pharmaceutical formulation, and/or medical device to administer the drug may be sterilizable. In various embodiments, one or more components of the drug depot, pharmaceutical formulation, and/or medical device to administer the drug are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot, pharmaceutical formulation, and/or one or more components of the device, including, but not limited to, gas sterilization, such as, for example, with ethylene oxide or steam sterilization.

In various embodiments, a kit is provided that may include additional parts along with the drug depot, pharmaceutical formulation, and/or medical device combined together to be used to implant the drug depot (e.g., ribbon-like fibers). The kit may include the drug depot device in a first compartment. The second compartment may include a canister holding the drug depot or pharmaceutical formulation and any other instruments needed for the localized drug delivery. A third compartment may include gloves, drapes, wound dressings and other procedural supplies for maintaining sterility of the implanting process, as well as an instruction booklet. A fourth compartment may include additional cannulas and/or needles. Each tool may be separately packaged in a plastic pouch that is radiation sterilized. A cover of the kit may include illustrations of the implanting procedure and a clear plastic cover may be placed over the compartments to maintain sterility.

Drug Delivery

In various embodiments, a method for delivering a statin into a target tissue site of a patient is provided, the method comprising inserting a cannula at or near a target tissue site and implanting the drug depot containing the statin at the target site beneath the skin of the patient. In various embodiments, to administer the drug depot to the desired site, first the cannula or needle can be inserted through the skin and soft tissue down to the target tissue site and the drug depot administered (e.g., injected, implanted, instilled, sprayed, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In various embodiments, the drug depot can be sutured to the target site or alternatively the drug depot can be implanted, without suturing. For example, in various embodiments, the drug depot can be a ribbon shaped depot and placed at the target site, before, during or after surgery.

In various embodiments, when the target tissue site comprises a spinal region, a portion of fluid (e.g., spinal fluid, etc.) can be withdrawn from the target site through the cannula or needle first and then the depot administered (e.g., placed, dripped, injected, or implanted, etc.). The target site will re-hydrate (e.g., replenishment of fluid) and this aqueous environment will cause the drug to be released from the depot.

Treating or treatment of a disease or condition refers to executing a protocol, which may include administering one or more drugs to a patient (human, other normal or otherwise), in an effort to alleviate signs or symptoms of the disease. Alleviation can occur prior to signs or symptoms of the disease or condition appearing, as well as after their appearance. Thus, "treating" or "treatment" may include "preventing" or "prevention" of disease or undesirable condition. In addition, "treating" or "treatment" does not require complete alleviation of signs or symptoms, does not require a cure, and specifically includes protocols that have only a marginal effect on the patient. "Reducing pain" includes a decrease in pain and does not require complete alleviation of pain signs or symptoms, and does not require a cure. In various embodiments, reducing pain includes even a marginal decrease in pain. By way of example, the administration of one or more effective dosages of the statin may be used to prevent, treat or relieve the symptoms of post-operative pain and/or inflammation incidental to surgery.

"Localized" delivery includes, delivery where one or more drugs are deposited within, at or near a tissue. For example, localized delivery includes delivery to a nerve root of the nervous system or a region of the brain, or in close proximity (within about 10 cm, or preferably within about 5 cm, for example) thereto. "Targeted delivery system" provides delivery of one or more drugs depots (e.g., gels or depot dispersed in the gel, etc.) having a quantity of therapeutic agent that can be deposited at or near the target tissue site as needed for treatment of pain and/or inflammation incidental to surgery.

FIG. 1 illustrates a number of common locations within a patient that may be subject to pain. It will be recognized that the locations illustrated in FIG. 1 are merely exemplary of the many different locations within a patient where pain may be experienced. For example, pain may occur at a patient's knees 21, hips 22, fingers 23, thumbs 24, neck 25, and spine 26. Thus, the patient may experience pain and/or inflammation in these and other areas.

The statin may be used for localized and/or targeted delivery to a patient to treat pain and/or inflammation associated with different diseases or condition such as for example, rheumatoid arthritis, osteoarthritis, spondilothesis, stenosis, sciatica, carpal/tarsal tunnel syndrome, lower back pain, lower extremity pain, upper extremity pain, cancer, tissue pain, pain associated with injury, surgery or repair of cervical, thoracic, and/or lumbar vertebrae or intervertebral discs, rotator cuff, articular joint, TMJ, tendons, ligaments, muscles, or the like.

Pain can be categorized into three groups: (1) acute pain; (2) continuous pain in terminally ill patients; and (3) other forms of chronic pain. In acute pain, a specific noxious stimulant of limited duration can be identified. Acute pain is often characterized by a distinct onset, usually with identifiable etiology such as trauma or surgery. In contrast to acute pain, neuropathic pain serves no beneficial purpose. Neuropathic pain results when pain associated with an injury or infection continues in an area once the injury or infection has resolved. Pain includes nociception and the sensation of pain, both of which can be assessed objectively and subjectively, using pain scores and other methods well known in the art.

In various embodiments, pain may include allodynia (e.g., increased response to a normally non-noxious stimulus) or hyperalgesia (e.g., increased response to a normally noxious or unpleasant stimulus), which can in turn be thermal or mechanical (tactile) in nature. In some embodiments, pain is characterized by thermal sensitivity, mechanical sensitivity and/or resting pain. In other embodiments, pain comprises mechanically-induced pain or resting pain. In still other embodiments, the pain comprises resting pain. The pain can be primary or secondary pain, as is well known in the art.

Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In various embodiments, the statin may be used to reduce, treat, or prevent sciatic pain and/or inflammation by locally administering the statin at one or more target tissue sites (e.g., nerve root, dorsal root ganglion, focal sites of pain, at or near the spinal column, etc.).

The statin may also be used in conjunction with other pain management medication. The term "pain management medication" includes one or more therapeutic agents that are administered to reduce, prevent, alleviate or remove pain entirely. These include anti-inflammatory agents, muscle relaxants, analgesics, anesthetics, narcotics, etc., or combinations thereof.

In various embodiments, the post-surgical pain or postoperative pain or surgery-induced pain, is accompanied by inflammation. Inflammation can be an acute response to trauma or surgery. When tissues are damaged, TNF-α attaches to cells to cause them to release other cytokines that cause inflammation. The purpose of the inflammatory cascade is to promote healing of the damaged tissue, but once the tissue is healed the inflammatory process does not necessarily end. Left unchecked, this can lead to degradation of surrounding tissues and associated pain. Thus, pain can become a disease state in itself. That is, when this pathway is activated, inflammation and pain ensue. Often a vicious and seemingly endless cycle of insult, inflammation, and pain sets in.

Figure 2:
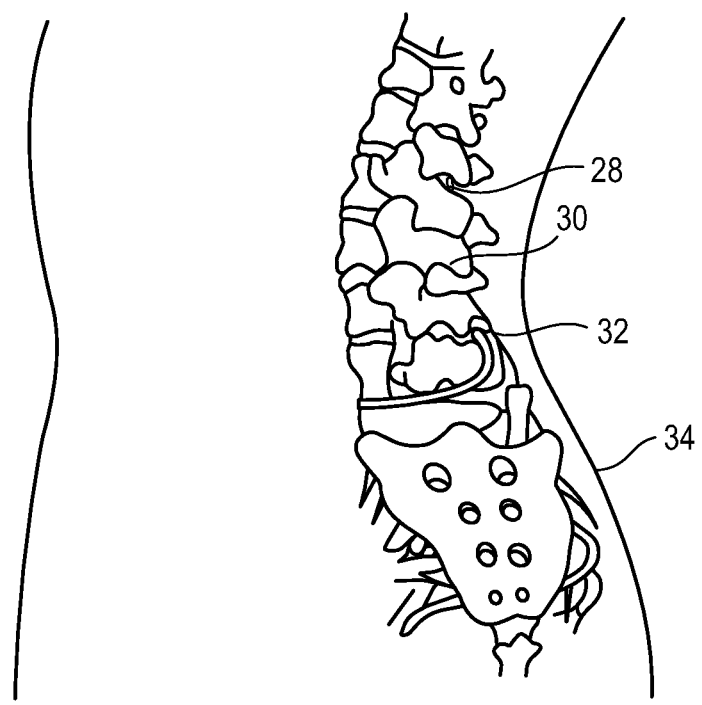
FIG. 2 illustrates a schematic dorsal view of the spine and sites where the parenteral statin formulation may be locally administered (e.g., injection, infusion, depot, etc.) to treat pain and/or inflammation associated with sciatica.

One exemplary embodiment where the depot is suitable for use in pain and/or inflammation management (e.g., post operative pain and/or inflammation management) is illustrated in FIG. 2. Schematically shown in FIG. 2 is a dorsal view of the spine and sites where the drug depot may be inserted using a cannula or needle beneath the skin 34 to a spinal site 32 (e.g., spinal disc space, spinal canal, soft tissue surrounding the spine, nerve root, etc.) and one or more drug depots 28 and 32 are delivered to various sites along the spine. In this way, when several drug depots are to be implanted, they are implanted in a manner that optimizes location, accurate spacing, and drug distribution, which can optimize statin treatment.

Although the spinal site is shown, as described above, the drug depot can be delivered to any site beneath the skin, including, but not limited to, at least one muscle, ligament, tendon, cartilage, spinal disc, spinal foraminal space, near the spinal nerve root, or spinal canal. In various embodiments, the drug depot containing a statin can be administered to the patient intra-operatively, intravenously, intramuscularly, SC, intrathecally, intradiskally, peridiskally, epidurally, perispinally, or parenterally or combinations thereof.

The term "patient" refers to organisms from the taxonomy class "mammalian," including but not limited to humans, other primates such as chimpanzees, apes orangutans and monkeys, rats, mice, cats, dogs, cows, horses, etc.

In various embodiments, a strategy of triangulation may be effective when administering multiple drug depot formulations. Thus, a plurality (at least two, at least three, at least four, at least five, at least six, at least seven, etc.) drug depots comprising the pharmaceutical formulations may be placed around the target tissue site (also known as the pain generator or pain generation site) such that the target tissue site falls within a region that is either between the formulations when there are two, or within an area whose perimeter is defined by a set of plurality of formulations.

Figure 3:
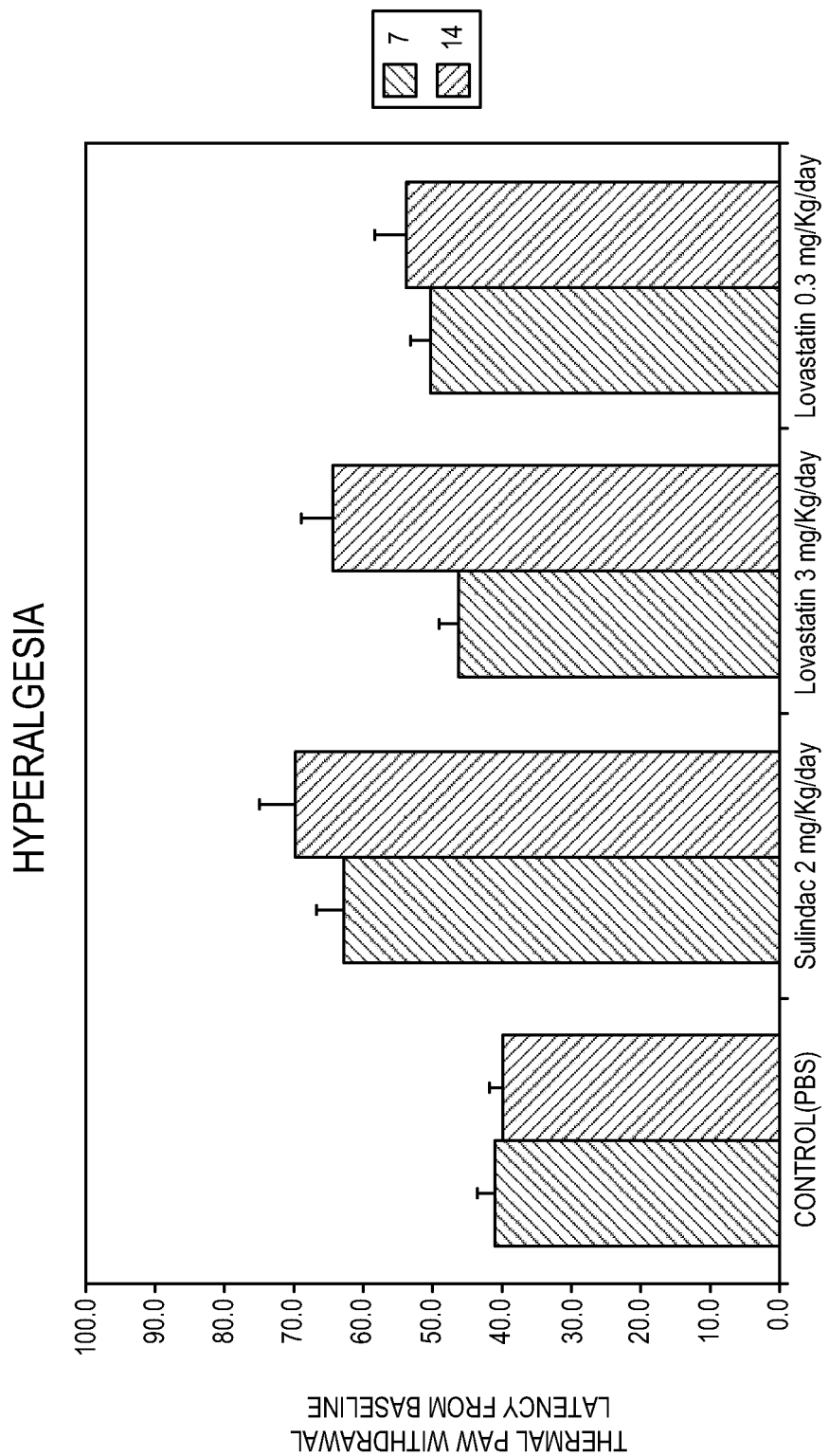
FIG. 3 shows the effect of a statin (lovastatin) at different doses on pain sensitivity as measured by paw withdrawal latency to thermal radiant heat stimuli, which is a widely used nociceptive measure to study the hyperalgesic mechanisms.

FIG. 3 shows the effect of a statin (lovastatin) at different doses on pain sensitivity as measured by paw withdrawal latency to thermal radiant heat stimuli, which is a widely used nociceptive measure to study the hyperalgesic mechanisms. Lovastatin was administered by intraperitoneal injection at a dose of 3 mg/kg/day or 0.3 mg/kg/day for 15 days and sulindac was administered by intraperitoneal injection at a dose of 2 mg/kg/day for 15 days. Paw withdrawal was measured when thermal radiant heat was applied and compared to the control, where the animals were given PBS vehicle, on days 7 and 14. The data show that lovastatin at a dose of 3 mg/kg/day or 0.3 mg/kg/day for 15 days and sulindac at a dose of 2 mg/kg/day for 15 days is effective at reducing pain. Sulindac 2 mg/kg/day for 15 days and lovastatin at doses of 3 mg/kg/day at day 14 were particularly effective. Lower dose lovastatin at 0.3 mg/kg/day at 7 days and 14 days showed similar reduction in pain.

Figure 4:
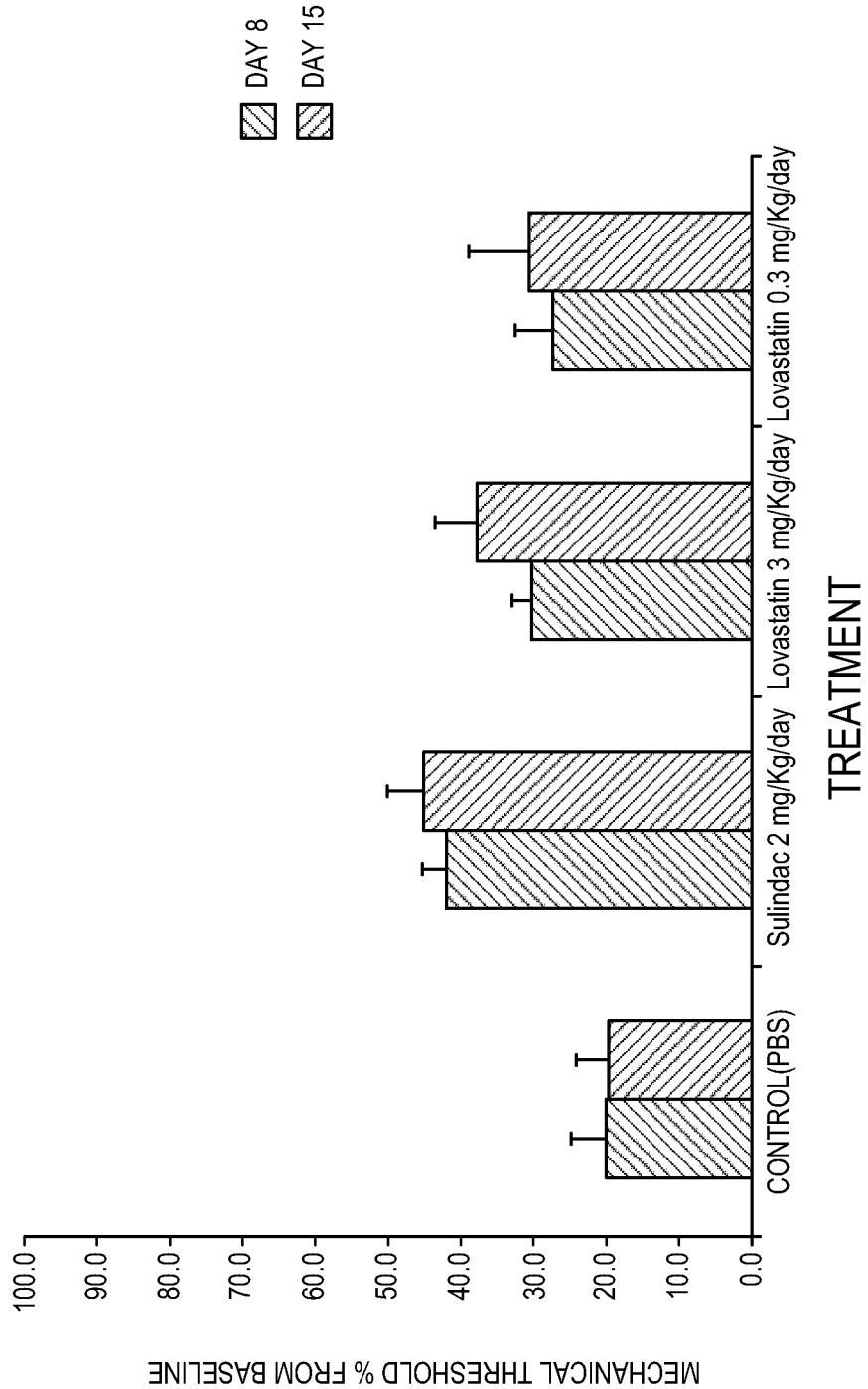
FIG. 4 shows the effect of a statin (lovastatin) at different doses on pain sensitivity as measured by the von Frey filament test widely used to determine tactile allodynia.

FIG. 4 shows the effect of a statin (lovastatin) at different doses on pain sensitivity as measured by the von Frey monofilament test (mechanical stimulation) widely used to determine tactile allodynia. The von Frey test utilizes monofilament fibers inserted into a holder that allow a scientist to exert a defined pressure on a punctiform area of the paw.

Figure 5:
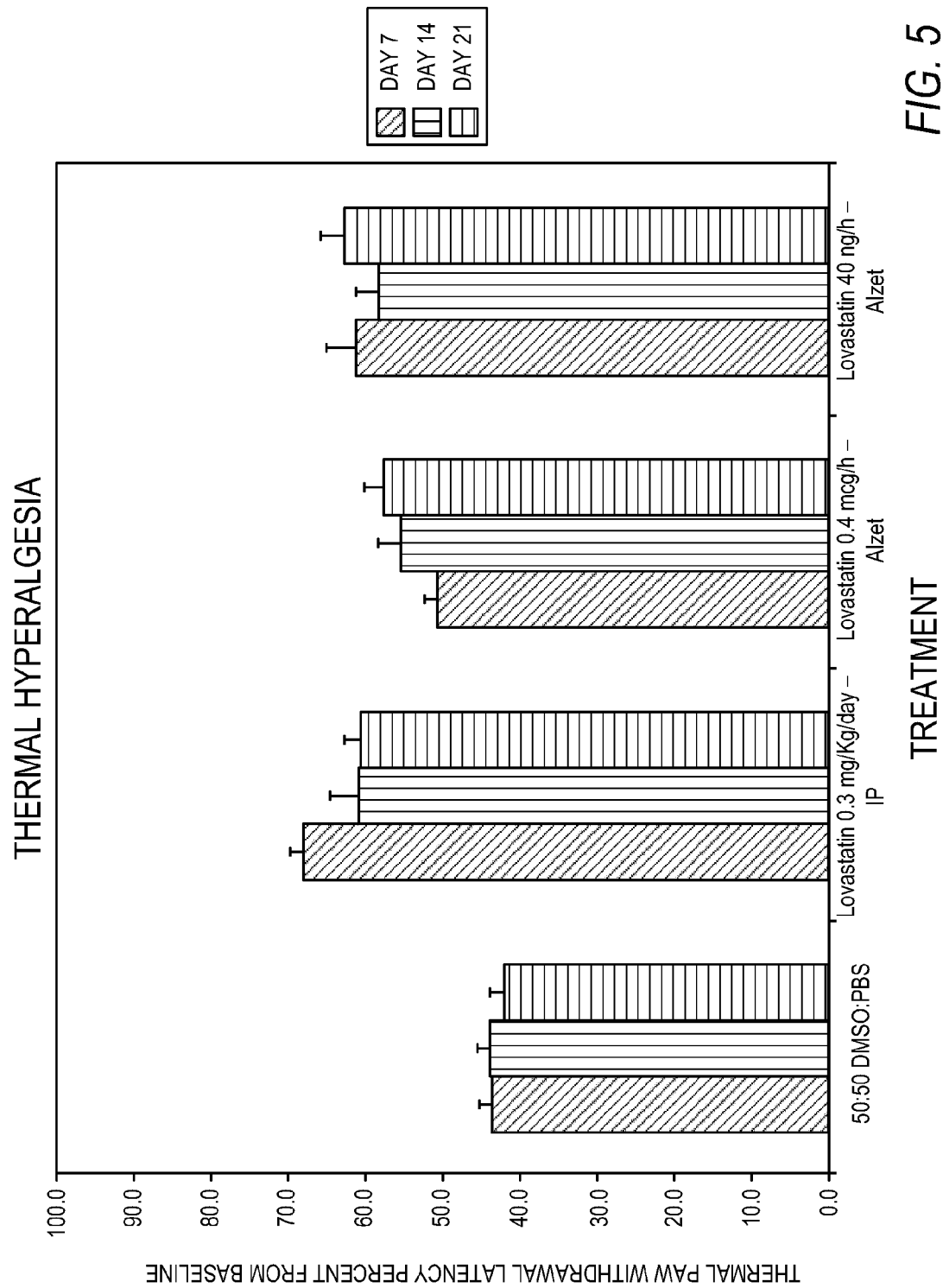
FIG. 5 shows the effect of a statin (lovastatin) at milligram, microgram, and nanogram doses on pain sensitivity as measured by paw withdrawal latency to thermal radiant heat stimuli, which is a widely used nociceptive measure to study the hyperalgesic mechanisms.
Figure 6:
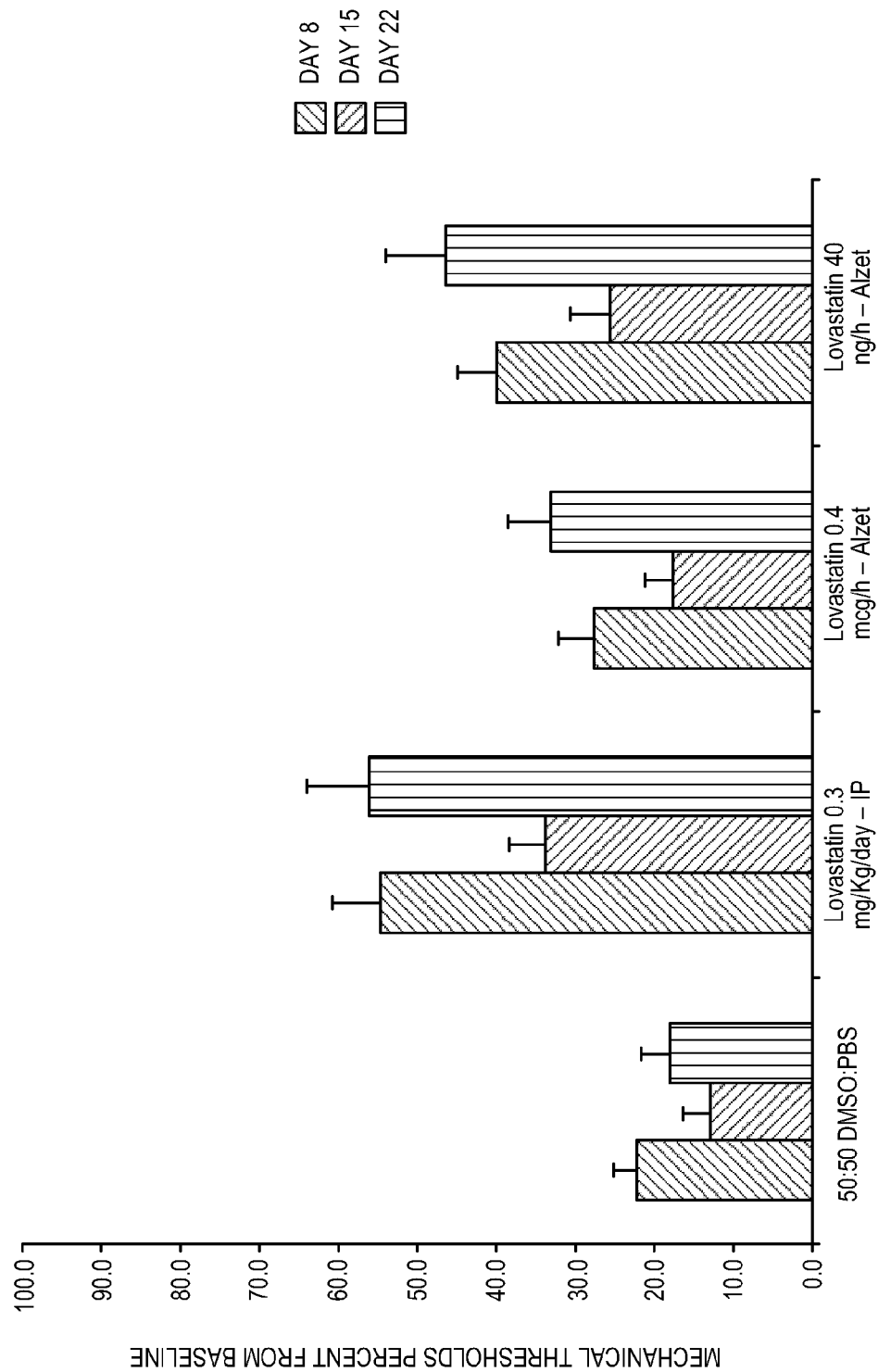
FIG. 6 shows the effect of a statin (lovastatin) at milligram, microgram, and nanogram doses on pain sensitivity as measured by the von Frey filament test widely used to determine tactile allodynia.

The animals are repeatedly mechanically stimulated with increasingly strong filaments to determine the threshold where nocifensive paw withdrawal response is reliably elicited. Lovastatin was administered by intraperitoneal injection at a dose of 3 mg/kg/day or 0.3 mg/kg/day for 15 days and sulindac was administered by intraperitoneal injection at a dose of 2 mg/kg/day for 15 days. Paw withdrawal was measured when mechanical stimulation was applied and compared to the control, where the animals were given PBS vehicle, at days 8 and 15. The data show that lovastatin at a dose of 3 mg/kg/day or 0.3 mg/kg/day for 15 days and sulindac at a dose of 2 mg/kg/day for 15 days is effective at reducing pain. Sulindac 2 mg/kg/day for 15 days and lovastatin at doses of 3 mg/kg/day at day 15 were particularly effective. Lower dose lovastatin at 0.3 mg/kg/day at days 8 and 15 showed similar reduction in pain. FIG. 5 shows the effect of a statin (lovastatin) at milligram, microgram, and nanogram doses on pain sensitivity as measured by paw withdrawal latency to thermal radiant heat stimuli, which is a widely used nociceptive measure to study the hyperalgesic mechanisms. FIG. 6 shows the effect of a statin (lovastatin) at milligram, microgram, and nanogram doses on pain sensitivity as measured by the von Frey filament test widely used to determine tactile allodynia.

Method of Making Statin Depots

In various embodiments, the drug depot comprising the statin can be made by combining a biocompatible polymer (as discussed above) and a therapeutically effective amount of a statin or pharmaceutically acceptable salt thereof and forming the implantable drug depot from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined an placed in a mold of the desired size and shape. In this way, polymeric regions, including barrier layers, lubricious layers, and so forth can be formed. If desired, the solution can further comprise, one or more of the following: a statin and other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: a statin, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, a statin may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with the therapeutic agent under conditions of lower temperature and mechanical shear, and the resulting mixture is shaped into the statin containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., a statin), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of different statins, because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or a viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., ribbon, pellet, strip, etc.) is cooled. Examples of cooling processes include air cooling and/or immersion in a cooling bath. In some embodiments, a water bath is used to cool the extruded depot. However, where a water-soluble therapeutic agent such as lovastatin is used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this release profile is not desired.

In various embodiments, the drug depot can be prepared by mixing or spraying the drug with the polymer and then molding the depot to the desired shape. In various embodiments, lovastatin is used and mixed or sprayed with the PLGA or PEG550 polymer, and the resulting depot may be formed by extrusion and dried.

Having now generally described the invention, the same may be more readily understood through the following reference to the following examples, which are provided by way of illustration and are not intended to limit the present invention unless specified.

EXAMPLES

The behavioral animal model of chronic constriction injury ("CCI") was chosen to evaluate the efficacy of lovastatin as a pain treatment. This model may mimic pain associated with sciatica in humans.

Example 1

Surgical Procedures

Twenty-eight male Wister rats (Charles River Laboratories, Wilmington, Mass.) weighing 300±26 g the day of surgery (Day 1) were used in this study. All experiments were conducted in accordance with the International Association for the Study of Pain guidelines and approved by the Institutional Animal Care and Use Committee at SRI International, Inc (Menlo Park, Calif.). CCI was induced according to the method of Bennett and Xie. Briefly, each animal was anesthetized by intraperitoneal (IP) injection of sodium pentobarbital at a dose of 60 mg/kg. The animal's common sciatic nerve was exposed and freed from adherent tissue at mid-thigh by separating the biceps femoris muscles by blunt dissection. Four loose ligatures were placed 1 mm apart, using chromic gut suture (4-0 absorbable suture; Jorgensen Laboratories, Inc., Loveland, Colo.).

Treatment Groups

Seven animals were randomly assigned to each treatment group. Animals were dosed for 15 days as indicated in Table 1.

TABLE 1

| | Dosing | | | |
|---|---|---|---|---|
| Group Number | Treatment | Dose | Concentration of inject, mg/mL | Comments |
| 1 | Vehicle (PBS [pH 8.0]) | 1 cc | NA | Vehicle |
| 2 | Sulindac | 2 mg/kg | 0.70 | Positive |

TABLE 1-continued

| | | Dosing | | |
|---|---|---|---|---|
| Group Number | Treatment | Dose | Concentration of inject, mg/mL | Comments |
| 3 | Lovastatin | 3 mg/kg | 1.05 | control; IP daily IP daily |
| 4 | Lovastatin | 0.3 mg/kg | 0.105 | IP Daily |

Example 2

Assessment of Behavior

Withdrawal latencies to a noxious thermal stimulus were measured according to the Hargreaves test using a plantar analgesia instrument (Stoelting, Wood Dale, Ill.) on Days −2 (baseline), 7, and 14. The radiant infrared heat source stimulus intensity was set to IR50 and the cut-off time was set at 15 seconds. Rats were placed on a glass platform and allowed to habituate to the testing chambers for a minimum of 15 minutes prior to each testing session. The thermal stimulus was applied to the plantar surface of the paw. Thermal thresholds were defined as the latency in seconds at the first pain behavior, which includes paw withdrawal, flinching, biting and/or licking of the stimulated paw. The readings for all animals were averaged and the mean and standard error of the mean (SEM) were determined for each treatment group.

The results are graphically shown in FIG. 3. This figure show the effect of a statin (lovastatin) at different doses on pain sensitivity as measured by paw withdrawal latency to thermal radiant heat stimuli, which is a widely used nociceptive measure to study the hyperalgesic mechanisms. Paw withdrawal was measured when thermal radiant heat was applied and compared to the control, where the animals were given PBS vehicle. The data show that lovastatin at a dose of 3 mg/kg/day or 0.3 mg/kg/day for 15 days and sulindac at a dose of 2 mg/kg/day for 154 days is effective at reducing pain. Sulindac 2 mg/kg/day at 7 and 14 days and lovastatin at a dose of 3 mg/kg/day at 14 days were particularly effective at reducing pain. Lower dose lovastatin at 0.3 mg/kg/day at 7 and 14 days showed similar reduction in pain.

Mechanical allodynia was measured using von Frey monofilaments (Stoelting, Wood Dale, Ill.) with varying stiffness (2.0-15.0 g) on Days −1 (baseline), 8, and 15 as described previously. Animals were placed on a perforated metallic platform and allowed to habituate to their surroundings for a minimum of 15 minutes before testing. The 50% paw withdrawal threshold response was determined by a sequential increasing and/or decreasing of the stimulus strength (the "up-down method" of Dixon). Each filament was applied with enough pressure to cause a buckling effect. Absence of a paw lifting/withdrawal response after 5 seconds prompted the use of the filament of next higher weight. Paw withdrawal indicating a positive response prompted the use of a weaker filament. After the initial response (i.e., paw withdrawal), the testing continued for four additional measurements and was used to calculate the response threshold. Four consecutive positive responses received a score of 0.25 g, and five consecutive negative responses (i.e., no paw withdrawal) received a score of 15 g. The 50% paw withdrawal threshold was calculated using the formula: $10^{(Xf+kd)}/10,000$, where Xf is the final von Frey filament used (log units), k is a value that analyzes the response pattern (taken from the table published by Chaplan et al.), and d is the mean difference between stimuli (log units). The mean and standard error of the mean (SEM) were determined for each treatment group.

The results are graphically shown in FIG. 4. This figure shows the effect of a statin (lovastatin) at different doses on pain sensitivity as measured by the von Frey filament test (mechanical stimulation) widely used to determine tactile allodynia. The data show that lovastatin at a dose of 3 mg/kg/day or 0.3 mg/kg/day for 15 days and sulindac at a dose of 2 mg/kg/day for 15 days is effective at reducing pain. Sulindac 2 mg/kg/day at 8 and 15 days and lovastatin at doses of 3 mg/kg/day at 15 days were particularly effective. Lower dose lovastatin at 0.3 mg/kg/day at and 15 days showed similar reduction in pain.

Example 3

Thermal hyperalgesia was performed using, among other things, 50:50 DMSO/PBS as the vehicle control, which consistently records a withdrawal time that is about 42% of per-operative baseline. The 0.3 mg/kg/day IP dose reduced this pain behavioral response at all days tested. After reducing this behavioral response to 68% on Day 7, this group held consistently at 61% for days 14 and 21. The high dose lovastatin pump group (0.4 mcg/hr; 10-fold reduction from 0.3 mg/kg/day) steadily improved during the course of the study, and by day 21 recorded a score that should be statistically equivalent to the other two statin groups. The low dose for the lovastatin group (100-fold decrease from the 0.3 mg/kg/day group) recorded showed consistent withdrawal scores near 60% of baseline on all testing days. These scores should be statistically equivalent to the 0.3 mg/kg/day group. This may indicate the upper-dose limit for this localized depot application. FIG. 5 graphically illustrates the effect of lovastatin at milligram, microgram, and nanogram doses on pain sensitivity as measured by paw withdrawal latency to thermal radiant heat stimuli.

Example 4

Mechanical allodynia: This behavioral assessment is always interesting in this model. Particularly interesting is the decrease in mechanical thresholds on day 15. 50:50 DMSO/PBS showed a severe reduction in mechanical allodynia over the course of this experiment. Lovastatin dosed at 0.4 mcg/hr is probably statistically equivalent to the vehicle control in reducing this pain response. Lovastatin at 0.3 mg/kg/day was able to reduce this pain behavioral response at all time points, and the 40 ng/hr group is probably statistically equivalent. FIG. 6 graphically illustrates the results of this experiment where the effect of lovastatin at milligram, microgram, and nanogram doses on pain sensitivity was measured using this model.

These experiments show that lovastatin is effective at reducing pain and/or inflammation.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating pain and/or inflammation from sciatica or spondylolisthesis in a patient in need of such treatment, the method comprising locally administering one or more drug depots comprising a therapeutically effective amount of a statin or pharmaceutically acceptable salt thereof, a therapeutically effective amount of a glial cell-derived neurotropic factor and a polymer having an average molecular weight of about 1,000 to about 10,000, a particle size of about 10 micrometers to about 250 micrometers and a L/G ratio of 65:35 having a duration of delivery of about 2 months at or near a target tissue site beneath the skin of the patient to treat sciatic or spondylolisthesis pain and/or inflammation, wherein the one or more drug depots release 0.1 mg/kg/day to about 3 mg/kg/day of the statin at or near the target tissue site and has a modulus of elasticity of about $1 \times 10^4$ to about $6 \times 10^5$ dynes/cm$^2$.

2. A method of treating pain and/or inflammation according to claim 1, wherein the statin is administered by local injection or infusion.

3. A method of treating pain and/or inflammation according to claim 1, wherein the drug depot is biodegradable and releases the statin or pharmaceutically acceptable salt thereof over a period of at least one day to 6 months.

4. A method of treating pain and/or inflammation according to claim 1, wherein the target tissue site comprises at least one muscle, ligament, tendon, cartilage, spinal disc, spinal foraminal space near the spinal nerve root, facet or synovial joint, or spinal canal.

5. A method of treating pain and/or inflammation according to claim 1, wherein the drug depot is administered at one or more target tissue sites at or near the sciatic nerve.

6. A method of treating pain and/or inflammation according to claim 1, wherein the statin comprises at least cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof.

7. A method of treating pain and/or inflammation according to claim 1, wherein the statin comprises lovastatin and is administered at a dose of about 0.3 mg/kg/day to about 3 mg/kg/day.

8. A method of treating pain and/or inflammation according to claim 1, wherein the drug depot releases 5%, 10%, 15%, 20%, 25%, 30%, 40%, 50%, 60%, 70%, 80%, 90%, 95%, or 99% of the statin or pharmaceutically acceptable salt thereof relative to a total amount of statin loaded in the drug depot over a period of one day to 6 months after the drug depot is administered to the target tissue site.

9. A method of treating pain and/or inflammation according to claim 1, wherein the drug depot releases 40 ng to about 5 mg of the statin or pharmaceutically acceptable salt thereof every hour to treat sciatic pain and/or inflammation.

10. A method of treating pain and/or inflammation according to claim 1, wherein the drug depot comprises at least one anti-inflammatory or analgesic agent, at least one anabolic or an anti-catabolic growth factor or a combination thereof.

11. A method of treating pain and/or inflammation according to claim 1, wherein the statin or pharmaceutically acceptable salt thereof is encapsulated in a plurality of depots comprising microparticles, microspheres, microcapsules, and/or microfibers suspended in a gel.

12. A method of reducing pain and/or inflammation from sciatica, or spondylolisthesis in a patient in need of such treatment, the method comprising locally administering one or more drug depots comprising a therapeutically effective amount of a statin or pharmaceutically acceptable salt thereof, a therapeutically effective amount of a glial cell-derived neurotropic factor and a biodegradable polymer having an average molecular weight of about 1,000 to about 10,000, a particle size of about 10 micrometers to about 250 micrometers and a L/G ratio of 65:35 having a duration of delivery of about 2 months at or near a target tissue site beneath the skin of the patient, wherein the one or more drug depots release 0.3 mg/kg/day to about 3 mg/kg/day of the statin at or near the target tissue site and has a modulus of elasticity of about $1 \times 10^4$ to about $6 \times 10^5$ dynes/cm$^2$.

13. A method of reducing pain and/or inflammation according to claim 12, wherein the statin is administered by local injection or infusion.

14. A method of reducing pain and/or inflammation according to claim 12, wherein one or more drug depots release an effective amount of a statin or pharmaceutically acceptable salt thereof over a period of one day to 6 months.

15. A method of reducing pain and/or inflammation according to claim 12, wherein the statin comprises at least cerivastatin, atorvastatin, simvastatin, pravastatin, fluvastatin, lovastatin, rosuvastatin, pitavastatin, velostatin, fluindostatin, dalvastain, or pharmaceutically acceptable salts thereof or a combination thereof.

16. A method of treating pain and/or inflammation from sciatica or spondylolisthesis in a patient in need of such treatment, the method comprising locally administering one or more drug depots consisting of a biodegradable polymer, a therapeutically effective amount of a statin or pharmaceutically acceptable salt thereof and a therapeutically effective amount of a glial cell-derived neurotropic factor, the biodegradable polymer having an average molecular weight of about 1,000 to about 10,000, a particle size of about 10 micrometers to about 250 micrometers and a L/G ratio of 65:35 having a duration of delivery of about 2 months at or near a target tissue site beneath the skin of the patient to treat pain and/or inflammation from sciatica or spondylolisthesis, wherein the one or more drug depots release 0.3 mg/kg/day to about 3 mg/kg/day of the statin at or near the target tissue site and has a modulus of elasticity of about $1 \times 10^4$ to about $6 \times 10^5$ dynes/cm$^2$.

17. A method according to claim 16, wherein the statin is cerivastatin, atorvastatin, simvastatin, pravastatin, fluvastatin, lovastatin, rosuvastatin, eptastatin, pitavastatin, velostatin, fluindostatin, dalvastain, or pharmaceutically acceptable salts thereof or a combination thereof.

18. A method according to claim 1 wherein the drug depot further comprising less than 20 wt % of methylpolyethylene glycol (mPEG).

19. A method according to claim 12 wherein the drug depot further comprising less than 10 wt % of methylpolyethylene glycol (mPEG).

20. A method according to claim 16 wherein the drug depot further comprising less than 5 wt % of methylpolyethylene glycol (mPEG).

* * * * *